US006251681B1

(12) United States Patent
Davies et al.

(10) Patent No.: US 6,251,681 B1
(45) Date of Patent: Jun. 26, 2001

(54) METHOD FOR THE DETECTION OF CANCER AND PREMALIGNANCY CONDITIONS THEREOF

(76) Inventors: Richard J. Davies, 21 Cameron Rd., Saddle River, NJ (US) 07458; Robert D. Juncosa, 588 Amberwood Dr., Yardley, PA (US) 19067

( * ) Notice: Subject to any disclaimer, the term of this patent is extended or adjusted under 35 U.S.C. 154(b) by 0 days.

(21) Appl. No.: 09/201,223

(22) Filed: Nov. 30, 1998

(51) Int. Cl.[7] .................................................. G01N 33/48
(52) U.S. Cl. ................................. 436/64; 436/63; 600/547
(58) Field of Search ........................ 436/63, 64; 128/734; 600/547

(56) References Cited

U.S. PATENT DOCUMENTS

| 4,537,203 | * | 8/1985 | Machida | 128/734 |
|---|---|---|---|---|
| 4,729,385 | * | 3/1988 | Juncosa | 128/734 |
| 4,862,092 | * | 8/1989 | Juncosa | 324/450 |
| 5,280,429 | * | 1/1994 | Withers | 364/413.15 |
| 5,526,808 | * | 6/1996 | Kaminsky | 128/632 |
| 5,720,296 | * | 2/1998 | Cha | 128/734 |
| 5,720,744 | * | 2/1998 | Eggleston | 606/40 |

* cited by examiner

Primary Examiner—Maureen M. Wallenhorst
(74) Attorney, Agent, or Firm—George J. Netter

(57) ABSTRACT

Tissue (10) from the colon or bowel is pretreated with a Ringers solution and mounted onto a ring (12) submerged in oxygenated Ringers solution (32), with first and second current electrodes (34,36) and first and second voltage electrodes (38,40) positioned within the solution (32) closely adjacent the tissue. A sequence of current pulses of different frequencies (44) covering a broad frequency range are applied via electrodes (34,36) to the tissue and corresponding impedance and resistance values are obtained (46). Comparison of impedance/resistance values establishes separate and distinct ranges of values for normal, cancerous and premalignant tissues.

11 Claims, 2 Drawing Sheets

METHOD FOR THE DETECTION OF CANCER AND PREMALIGNANCY CONDITIONS THEREOF

BACKGROUND

1. Field of the Invention

The present invention relates generally to the detection of cancerous tissues, and, more particularly, to a method and apparatus for detecting cancerous tissues of the epithelium of a human sigmoid colon and rectum, and, as well, detecting early changes in such epithelium which indicate the epithelium will eventually evolve into polyps or cancer.

2. Description of Related Art

It has been suggested in the past to determine the presence of certain cancerous tissue in a human by passing an electric current of predetermined value through suspected tissue and determining the electrical impedance of such tissue as compared to normal tissue. Similarly, it has also been suggested in the past that premalignant tissues which would, if nothing intervened, result in either polyps or cancerous tissue could be detectable by determining a specific change in tissue electrical impedance relative to the impedance of normal tissues.

It is generally considered in the prior art that human tissues composed of abnormal cells (i.e., tumor, carcinoma) exhibit an increased electrical impedance as compared to the impedance of the same tissues, if healthy. Exemplary of approaches to detection of cancerous tissues following these considerations are U.S. Pat. No. 4,729,385, PROBE AND METHOD OF USE FOR DETECTING ABNORMAL TISSUES by R. J. Davies and R. D. Juncosa and U.S. Pat. No. 4,690,152, APPARATUS FOR EPITHELIAL TISSUE IMPEDANCE MEASUREMENTS by R. D. Juncosa. Also, *Arch. Geschwulstforsch* 58: 105–111 (1988) discusses electrical parameters of the cervical epithelium, and *European Surgical Research* (22):86–92 (1990) is concerned with the bio-impedance of breast tumors.

In none of the known prior work has there been provided a fully satisfactory technique for determining when a tissue is cancerous by measuring its transepithelial electrical impedance. Moreover, even less correlation has been established in the past as to when a tissue that, by other tests, is not presently in a malignant stage, could by testing be found to determine or red flag the fact that it would eventually evolve into cancerous tissue.

SUMMARY OF THE INVENTION

It is a primary object and aim of the present invention to provide a method and apparatus for detecting the presence of cancerous tissues in a human bowel by measuring the transepithelial electrical impedance and comparing with a standard or normal value.

It is another object in accordance with the previous object to provide a method and apparatus for determining premalignancy of human bowel tissues by transepithelial impedance measurements.

In accordance with the practice of the present invention, there are provided method and apparatus for measuring the electrical impedance of samples of epithelium taken from the situs of a suspected tumor as well as at a site remote from suspect tissue. In the practice of this invention it has been found that the impedance ($X_N$) of normal bowel epithelium taken from an individual not having cancer of the bowel or colon is significantly higher than the impedance ($X_C$) measured across a tumor or measured across tissues immediately adjacent a tumor in an individual having cancer. Moreover, it has been found that the tissue impedance ($X_D$ at a distance from the tumor of an infected colon or bowel is greater than the control measurement $X_N$. At the same time, it is clear that the impedance measurement $X_C$ is dramatically less than that measurement taken on the same bowel or colon wall some distance away.

Measurement of tissue impedance in accordance with this invention is an electrical series circuit impedance measurement consisting of the Ringer solution impedance between voltage sensing probes, and the impedance of basal laminae and remaining connective tissue that physically lie in a path with the epithelium under examination. It is known that human tissues can be viewed electrically as being resistive and capacitive but have substantially zero inductive properties, so that the measured impedance when an alternating current is applied exhibits a so-called RC electrical impedance characteristic.

In accordance with the described invention, specimens of human sigmoid colon and rectum to be tested are surgically obtained and placed in an oxygenated Ringer solution during transport to the test site. Then, the tissue after being stretched over a ring-shaped mounting base is treated with a further Ringer solution. Immediately prior to electrical test, the tissue "cartridge" is once again bathed by oxygenated physiological saline.

While maintaining the tissue cartridge in contact with a flow of oxygenated Ringer solution of a prescribed temperature and at relatively low hydrostatic pressure, low resistance voltage sensing electrodes are located in slightly spaced relation (e.g., 2 mm) to the tissue surfaces. Transepithelial impedance is measured using a standard voltage-current clamp which permits compensation for resistance of fluid between the voltage sensing electrodes. A composite waveform consisting of a large number of different frequency, equal amplitude signals is applied to the epithelium. The signal is applied a plurality of times in two frequency ranges (low, LF; high, HF). Specifically, a given series of LF waveforms are applied, keeping the final reading and discarding the others. Similarly, a series of HF waveforms are applied keeping only the final impedance reading. At all other times, the tissue is maintained (clamped) at a predetermined voltage. The transepithelial impedance for test purposes is essentially the difference between the LF and HF measurements.

Physiologically, these results are consistent with the replacement of normally functioning epithelial cells by immature cells with different ionic transport function and consequent changed electrical characteristics. The human data in connection with the practice of the present invention indicates there is a higher epithelial resistance away from the tumor compared to a control, and as an epithelium close to or at a tumor is examined the resistance is lower than that of normal epithelium.

DESCRIPTION OF THE DRAWING

These and other objects and advantages of the present invention will become more readily apparent upon reading the following detailed description and upon reference to the attached drawings, in which.

DESCRIPTION OF A PREFERRED EMBODIMENT

Colon and rectal cancer at the present are known to produce death in a large number of cases (e.g., 58%) within five years after onset, making it the second most common cause of cancer death in the United States. When diagnosis is made sufficiently early that the cancer is restricted to the bowel wall (i.e., Duke's class A), the odds of survival increase to as high as 85% for a five year survival. The situation becomes still more favorable on being able to diagnose premalignant mucosa which would enable even still earlier treatment when cure is more likely. Moreover, identification of premalignant tissues would enable the initiation of intervention trials, such as dietary manipulation and chemoprevention in high-risk patients.

In regard to the ensuing description, examined tissues that were located at a tumor or within 5 cm of a tumor will be referred to as "suspicious", those located 5–30 cm from a tumor are termed "at risk", while control tissue is termed "normal".

Figure 1:
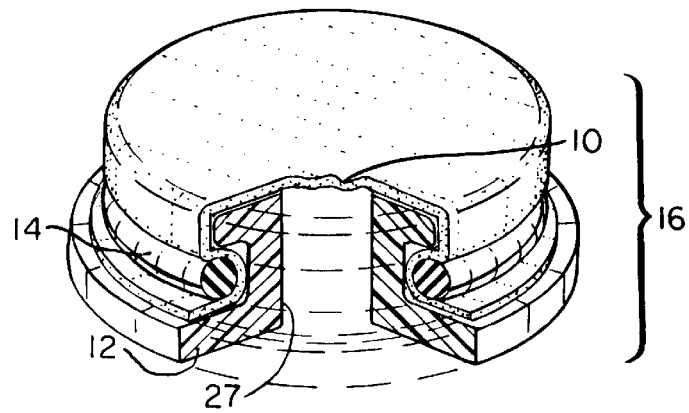
FIG. 1 is a perspective, partially sectional view of a tissue cartridge used in the practice of the present invention.

In connection with the testing procedure according to the present invention, reference is now made to the drawing and particularly FIG. 1. Specimens of tissues 10 to be examined as described are obtained surgically in accordance with known medical procedures and initially rinsed in a standard mammalian Ringer's solution ($NaCl$—$HCO_3$). The tissue is stretched over a relatively rigid plastic ring 12 (e.g., Lucite) and secured thereto by an elastic band 14 cut, for example, from surgical latex tubing to form a test cartridge 16. The cartridge is then placed in oxygenated Ringer's solution (95% $O_2$, 5% $CO_2$) for approximately 1 hour at a temperature of 22° Centigrade prior to electrical testing.

Figure 2:
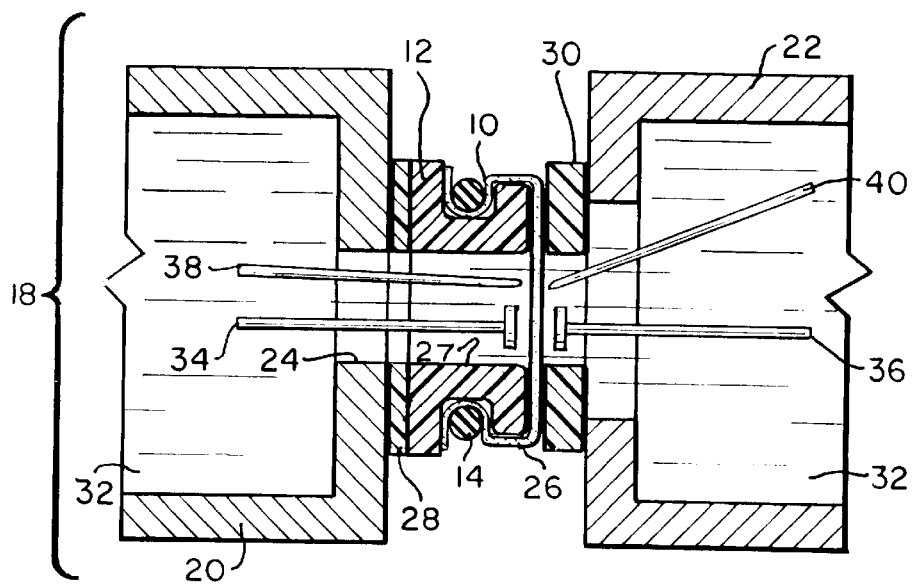
FIG. 2 is a sectional, schematic view of a tissue cartridge mounted for electrical testing.

Turning now to FIG. 2 a housing or holder 18 for a tissue cartridge includes first and second chambers 20 and 22, respectively, which can be moved toward and from each other as indicated by the arrows. Openings 24 and 26 in the respective chambers 20 and 22 are aligned and face one another with their cross-sectional dimensions being at least equal to the width of the ring 12 opening 27. The tissue cartridge 16 has annular gaskets 28 and 30 located on the opposite sides of the cartridge and compressed between the chambers 20 and 22 with openings 24, 26 and the ring opening 27 aligned.

The gaskets 28 and 30 are constructed of a relatively soft plastic material (e.g., Sylgart) which will create a liquid-tight seal. Also, gasket 30 on being soft and pliable has less of a tendency to tear the tissue 10 in the areas immediately adjacent tissue contact, which if it occurs, can result in erroneous electrical test results. Immediately prior to and throughout electrical testing, the tissue sample is bathed in oxygenated (95% $O_2$, 5% $CO_2$) physiological saline 32 at 37° C. supplied within both chambers 20 and 22 at a relatively low pressure. "Control" specimens of human colon were obtained from humans undergoing bowel resections for conditions other than bowel cancer, e.g., diverticulitis, volvulus, or trauma. These tissues on reaching the laboratory or other test site are similarly flushed with fresh oxygenated Ringer solution at room temperature (22° C.) and stripped of any underlying muscle, fat or connective tissue that may be present. Afterward, the tissues are cartridge-mounted in the manner already described and incubated in oxygenated NaCl Ringer for 2 hours prior to electrical testing.

Figure 3:
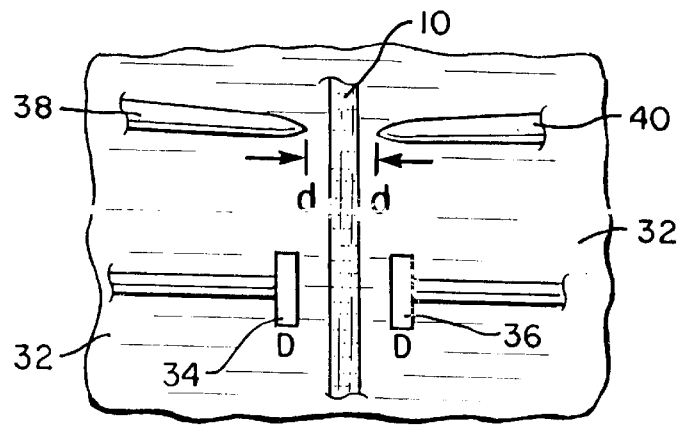
FIG. 3 is an enlarged detailed view of electrode positioning during testing.

Simultaneous reference to FIGS. 2 and 3 shows a sectional partially schematic depiction of the tissue specimen 10 in cross-section with two generally platelike current electrodes 34 and 36 held, respectively, in a relatively closely spaced (D) relation to the major opposite surfaces of the tissue specimens *e.g., 5 mm.). There will be some Ringer's solution 32 located between and in contact with the electrodes 34 and 36 as well as the opposite surface of the tissue. The purpose of the current electrodes in having a generally platelike geometry is to provide a relatively equal and uniform current in the tissue during electrical test.

Voltage sensing electrodes 38 and 40 are located in an even more closely spaced relation (d) to the opposite surfaces of the tissue sample (e.g., 2 mm) with the Ringer's solution 32 forming a thin film between the voltage electrodes and the facing tissue surface. Also, the tissue will typically include a certain amount of basal laminae and connective tissue that remains, even though such materials are removed and discarded for the most part. Accordingly, voltage measurements taken across electrodes 38 and 40 can be considered as taken across a series circuit consisting of the electrical impedance of the intervening solution 32, basal laminae and connective tissue (10) lying in a path between these electrodes.

During actual electrical tissue testing to be described, a continuous flow of prewarmed and oxygenated Ringer's solution 32 is applied to the opposite surfaces of the tissue specimen 10 at low hydrostatic pressure. For all tests from which data is given herein, the tissue "window" had an area of 0.0105 $cm^2$.

It has been found advisable after the physical preparation and mounting of tissue specimen 10 as described, that the current electrodes 34 and 36 be shorted together at all times other than during the taking of actual impedance measurements and during brief periods when current pulses are applied across the tissue for monitoring conductance by switch 42.

Figure 5:
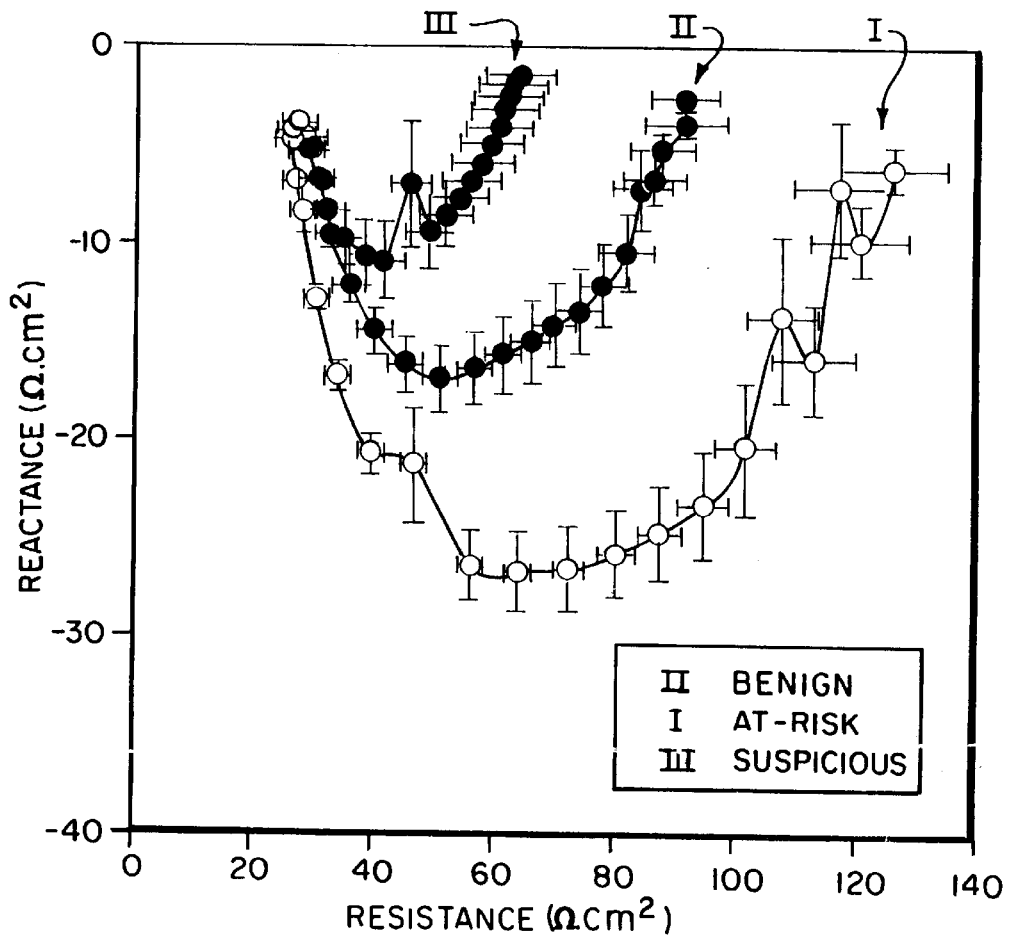
FIG. 5 is a graph of impedances measured in accordance with this invention for benign, diseased and premalignant tissues.

For actual electrical test, the current electrodes are released from their short-circuit relation and interconnected with a variable frequency alternating current source 44 which provides first a sequential set of different relatively low frequency waveforms (LF) followed by a further set of relatively high frequency waveforms (HF). Voltage readings for each waveform are taken by probes 38 and 40 for measurement at 46 and after being acted upon by an A/D converter 48 provide individual impedance readout values by a graph printer 50 forming an impedance resistance profile for the tissue samples (FIG. 5). Each of the two frequency ranges (LF,HF) in practice have during actual runs included 53 different frequencies so that in the test there were a total of 106 different measurements taken at 106 different frequencies. In actual test runs the voltage frequencies encompassed 0.4 –5517 Hertz.

It has been found advisable to use a particular test procedure in order to insure that both the equipment and tissues are in a relatively steady state condition before considering measurement data to be reliable. Specifically, with a tissue sample short-circuited sufficiently long to come to a steady state, four sets of sequential LF waveforms are applied throwing away the first three sets of measurements and keeping (i.e., printing out) the fourth or last set of measurements. Similarly, four sets of HF waveforms are then applied and only the last or fourth set of readings from the A/D converter are kept.

With reference now particularly to FIG. 5, there is shown in graphical form the results of control (i.e., cancer free) and diseased tissue testing. The curve identified as I ("suspicious") depicts impedance data taken at a suspected tumor or within 5 cm. of the tumor. Graph trace II ("normal") consists of data taken from patients undergoing surgery for other than cancer, and accordingly, serves as a control measurement. Finally trace III ("at risk") consists of data taken at a spacing of 5–30 cm. from a tumor.

It is to be noted first of all that the "normal" curve II has a higher impedance than the readings I taken at the tumor or within 5 cm. ("suspicious"). Moreover, the "at risk" curve I exhibits even higher impedance than the normal curve readings.

Based upon a large number of tests as described herein, 95% of patients with benign or normal colons had tissue samples with resistances between 37–87 $\Omega.cm^2$ with a mean of 61.7±25.2 $\Omega.cm^2$ (means±standard deviation). In comparison, patients having "suspicious" colons show tissue resistance in the range of 19–55 $\Omega.cm^2$ and "at risk" colons with a resistance range 61–139 $cm^2$.

Figure 4:
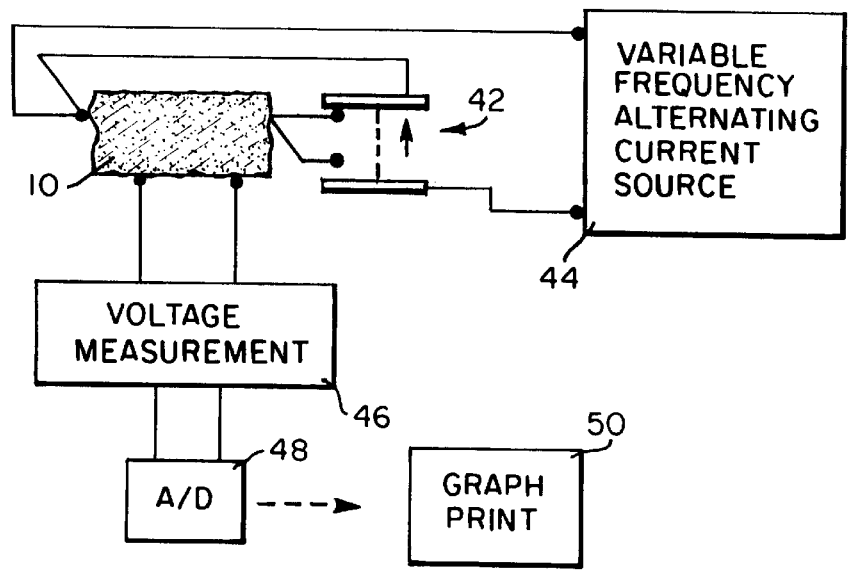
FIG. 4 is an electrical schematic of test apparatus used herein.

In accordance with the practice of the invention, a given tissue examination will provide an impedancegraph corresponding to one of the three (I, II, III) impedance/resistance plots shown in FIG. 4 with the ranges of individual impedance values indicated by the error bars. A patient with a "normal" impedance profile would not require additional testing while an "at risk" profile would result in additional testing, and a "suspicious" showing would lead to biopsy or surgery.

Although the invention has been described in connection with a preferred embodiment, it is understood that those skilled in the appertaining arts may contemplate changes coming within the spirit of the invention as disclosed and within the ambit of the appended claims. For example, a colonoscope could be modified to make real time impedance measurements to identify regions of abnormality which would require biopsy.

What is claimed is:

1. A method of determining a cancerous condition of a human bowel or colon epithelium, comprising the steps of:
   obtaining a test tissue sample from the bowel or colon;
   measuring resistance values of the test tissue sample at a plurality of different alternating voltage frequencies lying in the range of about 0.4–4417 Hz; and
   determining the median of the test sample measured resistance values;
   wherein when the median of the tissue sample resistance values is between 19–55 $\Omega.cm^2$ the test sample is indicated as cancerous.

2. A method as in claim 1, in which when the median of the test sample resistance values is between about 61–139 $\Omega.cm^2$ the test sample is indicated to be in a premalignant state.

3. A method as in claim 1, including the further step of shorting out the test tissue sample prior to and while resistance measuring takes place.

4. A method as in claim 1, in which each measuring step includes a plurality of sequentially taken sets of resistance measurements with only the last set being kept and the receding sets discarded.

5. A method as in claim 1, including the further step of applying $NaCl-HCO_3$ solution to opposite surfaces of the tissue sample during resistance measuring.

6. A method as in claim 5, in which the measuring step includes measuring the resistance of a series circuit consisting of a quantity of $NaCl-HCO_3$ solution in contact with one tissue sample surface, the tissue sample, and a further quantity of $NaCl-HCO_3$ solution in contact with an opposite surface of the tissue sample.

7. A method as in claim 5, in which the $NaCl-HCO_3$ solution is oxygenated by a solution consisting of 95% oxygen and 5% $CO_2$ at about 22° C.

8. A method as in claim 1, in which each measuring step is accomplished over a fixed predetermined tissue area.

9. A method as in claim 8, in which the predetermined tissue area is 0.501 $cm^2$.

10. Method of testing a predetermined test area of human tissue of the colon or bowel epithelium for a proclivity to become cancerous if nothing intervenes, comprising the steps of:
    passing a plurality of separately equal amplitude electric current pulses through the tissue, each pulse being of a different frequency;
    measuring a voltage drop across the predetermined area of tissue produced by each current pulse;
    determining a corresponding resistance value for each voltage drop measurement and the median value of all such resistance values;
    wherein when the median of the resistance values is between 61–139 $\Omega.cm^2$, the tissue is premalignant.

11. Method as in claim 10, in which the current pulse frequencies range from 0.4–5517 $H_z$.

* * * * *